US012397318B2

(12) United States Patent
Chen et al.

(10) Patent No.: US 12,397,318 B2
(45) Date of Patent: Aug. 26, 2025

(54) ULTRASONIC TRANSDUCER HEALTH STATUS MONITOR

(71) Applicant: Honeywell International Inc., Morris Plains, NJ (US)

(72) Inventors: Longfei Chen, Shanghai (CN); Bin Sai, The Hague (NL); Binbing Liu, Shanghai (CN)

(73) Assignee: Honeywell International Inc., Charlotte, NC (US)

( * ) Notice: Subject to any disclaimer, the term of this patent is extended or adjusted under 35 U.S.C. 154(b) by 1133 days.

(21) Appl. No.: 17/025,685

(22) Filed: Sep. 18, 2020

(65) Prior Publication Data
US 2022/0088636 A1 Mar. 24, 2022

(51) Int. Cl.
*B06B 1/02* (2006.01)
*B06B 1/06* (2006.01)
(Continued)

(52) U.S. Cl.
CPC .......... *B06B 1/0215* (2013.01); *B06B 1/067* (2013.01); *G01F 1/662* (2013.01); *G01F 15/185* (2013.01);
(Continued)

(58) Field of Classification Search
CPC ... B06B 1/067; B06B 1/0215; B06B 2201/40; B06B 2201/70; B06B 2201/76;
(Continued)

(56) References Cited

U.S. PATENT DOCUMENTS 6,766,276 B1 7/2004 Dury
2008/0139974 A1* 6/2008 Da Silva ................ A61B 8/546
601/3

(Continued)

FOREIGN PATENT DOCUMENTS

JP S52124175 A 10/1977
JP S6031160 B2 7/1985

OTHER PUBLICATIONS

Park, Gyuhae, et al., "Piezo-Sensor Self-Diagnostics Using Electrical Impedance Measurements," Engineering Sciences & Applications, 2004, 17pgs, Los Alamos National Laboratory, USA.
(Continued)

*Primary Examiner* — Emily P Pham
*Assistant Examiner* — Monica Mata
(74) *Attorney, Agent, or Firm* — John Maldjian, Esq.; Stevens & Lee PC (57) ABSTRACT

An ultrasonic-based system includes a transmitter and receiver, an ultrasonic transducer including piezoelectric element having a matching layer thereon connected to the transmitter. A controller is coupled to the transmitter. The transmitter is for driving the piezoelectric element with a pulsed electrical signal, where the piezoelectric element transmits a transmit ultrasonic signal. A current/voltage measurement circuit is coupled to sense a current or voltage in the transmitter. The controller is for implementing an algorithm for an ultrasonic transducer monitoring method including comparing an amplitude of the pulsed signal to a predetermined limit. When the pulsed signal is determined to be outside the limit, an impedance of the piezoelectric element is determined to be abnormal. When the pulsed signal is within the limit, the amplitude of the received signal is compared to a lower limit, which when below
(Continued)

results in determining a cleaning operation for the ultrasonic transducer is needed.

18 Claims, 5 Drawing Sheets

(51) Int. Cl.
　　　G01F 1/66　　　(2022.01)
　　　G01F 15/18　　(2006.01)
　　　G01N 29/48　　(2006.01)
　　　G01R 15/20　　(2006.01)
　　　G01S 7/52　　　(2006.01)
　　　G01S 15/89　　(2006.01)
　　　A61B 8/00　　　(2006.01)
(52) U.S. Cl.
　　　CPC .......... *G01N 29/48* (2013.01); *G01R 15/202* (2013.01); *G01S 7/5202* (2013.01); *G01S 7/52023* (2013.01); *G01S 15/8906* (2013.01); *A61B 8/4477* (2013.01); *A61B 8/54* (2013.01); *A61B 8/56* (2013.01); *B06B 2201/40* (2013.01); *B06B 2201/70* (2013.01); *B06B 2201/76* (2013.01)

(58) Field of Classification Search
　　　CPC ..... G01F 1/662; G01F 15/185; G01R 15/202; G01S 7/5202; G01S 7/52023; G01S 15/8906; A61B 8/54; A61B 8/56; A61B 8/4477
　　　USPC ............................................. 310/316.01, 316
　　　See application file for complete search history.

(56) References Cited

U.S. PATENT DOCUMENTS

| | | | |
|---|---|---|---|
| 2013/0133408 A1* | 5/2013 | Lang | G10K 11/002 73/64.53 |
| 2019/0068068 A1* | 2/2019 | Liu | H02M 1/0025 |
| 2019/0170550 A1* | 6/2019 | Sai | G01P 5/245 |
| 2020/0077892 A1* | 3/2020 | Tran | A61B 5/1117 |

OTHER PUBLICATIONS

Extended European Search Report mailed Feb. 18, 2022, issued in connection with corresponding EP Application No. 21195633.9 (6 pages total).

* cited by examiner

ULTRASONIC TRANSDUCER HEALTH STATUS MONITOR

FIELD

Disclosed aspects relate to ultrasonic transducer-based systems and apparatus that have at least one ultrasonic transducer.

BACKGROUND

Ultrasonic-based systems and apparatus having at least one ultrasonic transducer have applications including as fluid flowmeters, for oil and gas movement and transportation, for non-destructive testing (NDT) devices, and for medical applications including imaging for health monitoring. An ultrasonic transducer is known to comprise at least one piezoelectric element, where the piezoelectric element can include a front impedance matching layer and backing layer, and a housing in the front that can be a semi-opened housing or a fully closed housing. The performance of an ultrasonic transducer is generally most sensitive to a performance change by its piezoelectric element(s). Ultrasonic transducers may also include encapsulation for safety and/or application requirements, with the piezoelectric elements generally being encapsulated by a polymer-based adhesive material which results in no access to the piezoelectric element(s) without damaging the encapsulation.

Regarding flowmeters, in a variety of industries that involve the flow of a product, it is needed to be able to accurately measure the amount of product that is flowing at any given time. There are several different types of known flowmeters. Such known flowmeters include mechanical flowmeters (e.g. a piston meter, a Woltmann meter or a jet meter, which all measure fluid flow through some mechanical means), a vortex flowmeter (where vortices are generated by obstructing part of the fluid path, producing a voltage pulse, the frequency of which can be measured and hence flow can be determined), magnetic flowmeters (potential difference of a conducting fluid, as a result of an applied magnetic field, is measured and flow can be determined), and turbine as well as rotary flowmeters. There are also known to be static (meaning no moving parts) flowmeters which include ultrasonic flowmeters (USMs).

USMs are becoming popular for fluid flow metering because of their capability to measure a wide range of different flow rates, cause minimal pressure drops, and they also have no-moving parts thus providing less mechanical maintenance and better reliability as compared to most conventional flowmeter types. A key hardware component in the USM is an ultrasonic transducer, also known as an ultrasonic sensor, that comprises piezoelectric element(s) that comprises a piezoelectric crystal or a piezoelectric ceramic, typically comprising lead zirconate titanate (PZT). As known in physics the piezoelectric effect is the ability of certain materials to generate an electric charge responsive to an applied mechanical stress, as well as the reverse process.

Although USM's can include a single ultrasonic transducer, USMs generally include at least one pair of encapsulated ultrasonic transducers also known as 'potted' ultrasonic transducers. Encapsulated refers to the ultrasonic transducer being encased within an adhesive material, that as noted above is generally a polymer-based material. In operation of the USM the ultrasonic transducers operate by converting electrical energy supplied in the form of a pulsed electrical drive signal, where the ultrasonic transducer converts the electrical energy received into an ultrasonic signal which is transmitted and directed at the fluid being measured, and vice-versa when used as an ultrasonic receiver.

As noted above, USMs may include a housing, and within the housing there may be a printed circuit board (PCB) that includes a controller, such as a microcontroller unit (MCU) or digital signal processor, and other electronics, where the controller is generally either battery-powered and/or external line powered. The electronics can include a radio frequency (RF) unit including a transmitter and receiver coupled to an antenna (generally positioned outside of the housing) for providing wireless communications for the USM. The USM includes an ultrasonic transducer pair comprising a first and a second ultrasonic transducer. In one conventional ultrasonic transducer arrangement the transducers are configured on the same side of the pipe to produce a V-shaped ultrasonic signal path using a single reflection off the pipeline after passing through the fluid. Another known ultrasonic transducer arrangement is a direct transit path type that does not involve any signal reflection. There is a plurality of other known transducer arrangements, and the number of ultrasonic transducers can total up to about 16 or even more, the number ultrasonic transducers generally depending on the pipe diameter and cost constraints.

In each measurement cycle for the USM, enabled by a multiplexer that can be provided on the PCB that is communicatively coupled to be controlled by the controller, the first ultrasonic transducer works as a transmitter for transmitting ultrasonic waves, and the second ultrasonic transducer works as an ultrasonic receiver. The ultrasonic transducers then can be switched to exchange roles, so that the first ultrasonic transducer works as an ultrasonic receiver and the second transducer works as an ultrasonic transmitter.

USMs measure the velocity of flow by analyzing the interaction of the transmitted ultrasonic (or acoustic) waves with the moving fluid. Two of the most common types of USMs are a Doppler (reflection) flowmeter, and a transit time (time-of-flight) flowmeter. With the measured velocity, USMs can calculate the volumetric flowrate of a fluid flowing through knowing the cross-sectional area of the pipe.

The coupling of energy between an ultrasonic transducer and some fluid transmission mediums (e.g. air or other gas, or water) is known to be maximized when the fluid medium and the ultrasonic transducer have a matched specific acoustic impedance. Ultrasonic transducers may include an impedance matching layer for more efficiently coupling of the ultrasonic energy transmitted into the fluid as well as the ultrasonic energy received by the ultrasonic transducer after passing through the fluid. The ultrasonic matching layer is a passive layer which is generally affixed to the front face of the ultrasonic transducer. A damping layer may also be provided on the ultrasonic transducer on a side opposite the matching layer.

SUMMARY

This Summary is provided to introduce a brief selection of disclosed concepts in a simplified form that are further described below in the Detailed Description including the drawings provided. This Summary is not intended to limit the claimed subject matter's scope.

Disclosed aspects recognize the performance of an encapsulated ultrasonic transducer or an encapsulated ultrasonic transducer pair in an ultrasonic transducer-based system or apparatus and the ultrasonic transducers' useful lifespan are influenced by the encapsulated piezoelectric elements, and the electrical joint connections between the electrodes on the piezoelectric element(s) and the outside world. Such ultrasonic transducers as noted above may include a matching layer and a damping layer on the piezoelectric element(s). The encapsulation renders the ultrasonic transducer unable to be repaired or maintained without removing/breaking the encapsulation. In order to improve the reliability of an ultrasonic transducer-based system or apparatus having encapsulated ultrasonic transducer(s), disclosed aspects include health condition monitoring for encapsulated ultrasonic transducer(s) with predicative maintenance that removes the conventional need to remove the ultrasonic transducer(s) from their application for repair or for maintenance.

Moreover, it is recognized in the case of USMs where ultrasonic transducer pairs are installed on a pipe section for operation in the field for measuring fluid flow, a frequent failure mode is known to be ultrasonic transducer's piezoelectric element deformation and/or ageing, including for the commonly used PZT material. The other failure mode is the matching layer becoming contaminated by a material/substance that is carried within the fluid flowing within the pipe. It is known in the art to not be able to distinguish between these two different USM failure modes. A third failure mode for USMs is regarding their electrical joints to the electrodes of the piezoelectric element(s), where the wires may not be properly soldered or may become loose on the electrodes, that as a result may change in position or the wires may become detached due to a strain force, piezoelectric element vibration itself, or due to external vibrations propagating on the pipe.

Moreover, for conventional methods of monitoring the health status of the ultrasonic transducers of an ultrasonic-based systems or apparatus, such as an USM, the only signal being analyzed is the receiver side signal. For a USM there may be more than 1 pair of ultrasonic transducers, and/or for an USM even if it has a single-pair of ultrasonic transducers when it supports more than 1 channel. A channel is defined herein and as used in this art refers to an ultrasonic signal transmitted at an upstream direction e.g., ultrasonic transducer A to ultrasonic transducer B and the second channel is at a downstream direction (i.e., ultrasonic transducer B to ultrasonic transducer A), where the USM has at least one path.

For example, if one finds that the amplitude of the receiver side signal of one channel is significantly smaller as compared to the amplitude of the receiver side signal of a channel of another channel/path where a different pair of ultrasonic transducers are installed, then one can conclude that the pair of ultrasonic transducers being evaluated is not functioning properly. If the amplitude of the receiver side signal is significantly smaller than its historical signal level, then one can also conclude that the pair of ultrasonic transducers is not functioning properly. However, this known monitoring method cannot identify the cause of the signal attenuation that is needed to take a corrective/remedial action.

One disclosed embodiment comprises an ultrasonic-based system that includes a transmitter and receiver, and an ultrasonic transducer comprising at least one piezoelectric element having a matching layer thereon connected to at least the transmitter. A controller is coupled to the transmitter. The transmitter is for driving the ultrasonic transducer with a pulsed electrical signal, and in response the ultrasonic transducer transmits a transmit ultrasonic signal. A current or voltage measurement circuit is coupled to sense a current or a voltage in the transmitter. The controller is for implementing an algorithm for an ultrasonic transducer monitoring method that includes comparing an amplitude of the pulsed signal to at least one predetermined limit. When the pulsed signal is determined to be outside the predetermined limit, an impedance of the piezoelectric element is determined to be abnormal. When the pulsed signal is found to be within the predetermined limit, the amplitude of the received signal is then compared to a lower limit, which when below the lower limit results in determining that a cleaning operation for the matching layer is needed.

DETAILED DESCRIPTION

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

Figure 1A:
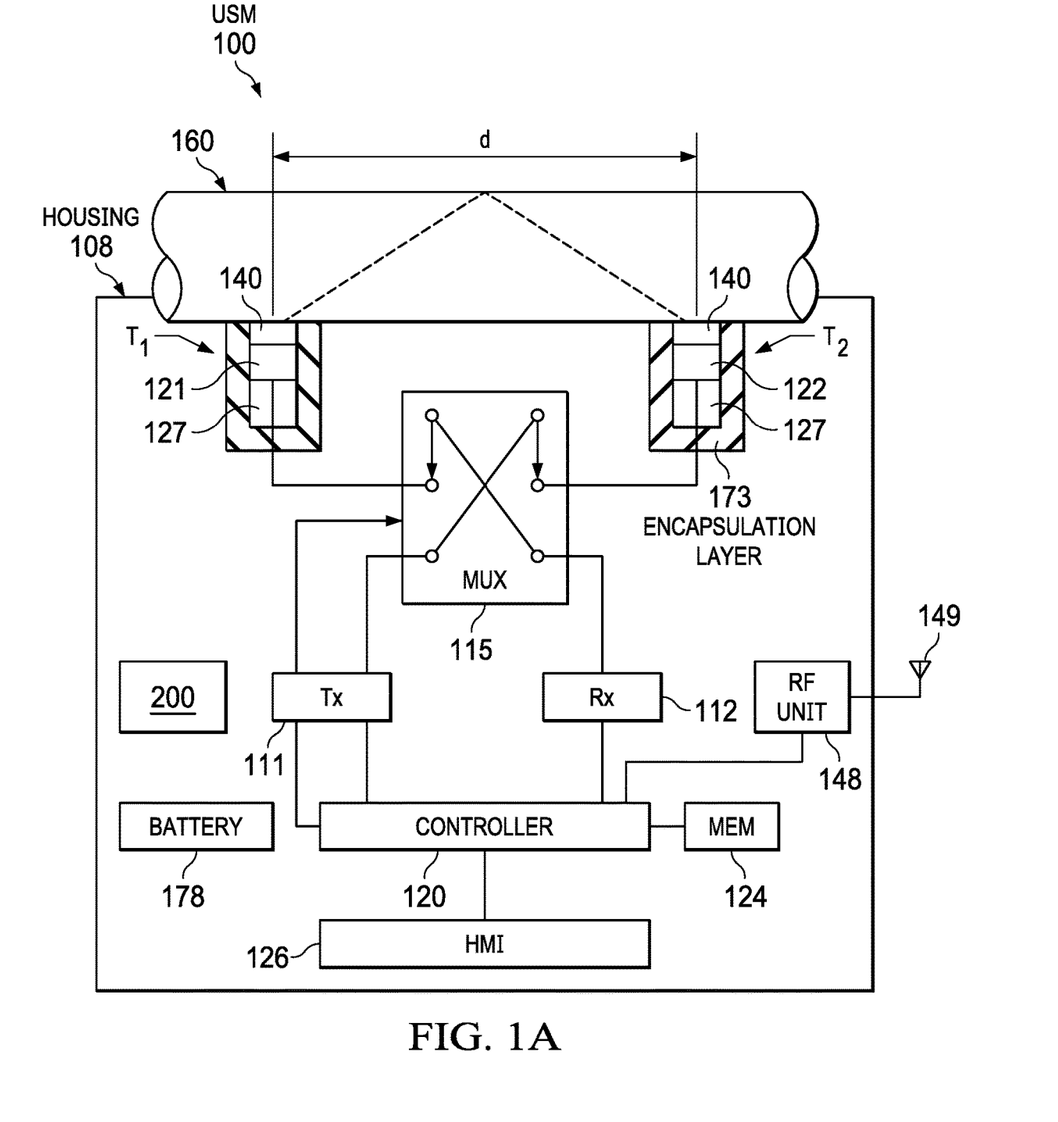
FIG. 1A is block diagram depiction of an example USM shown installed on a pipe section of a pipeline for flow measurements of a fluid flowing through the pipe section, where the USM includes an ultrasonic transducer pair including a first and a second ultrasonic transducer that together implement indirect path (reflective path) sensing, where the USM is shown including a current measurement circuit coupled to the transmitter, according to an example aspect.

FIG. 1A is block diagram depiction of an example USM 100 shown installed for flow measurements of a fluid flowing in a pipe section of a pipeline 160, where the USM 100 includes an ultrasonic transducer pair comprising a first and a second ultrasonic transducer shown as $T_1$ and $T_2$ each comprising at least one piezoelectric element shown as 121 for $T_1$ and 122 for $T_2$, where $T_1$ and $T_2$ together implement indirect path (reflective path) sensing. As noted above, another known ultrasonic transducer arrangement is a direct transit path type (i.e., face-to-face) that does not involve any ultrasonic reflection, and there can also be another type of single transducer that provides both Tx/Rx that utilizes a single reflective path.

Figure 2:
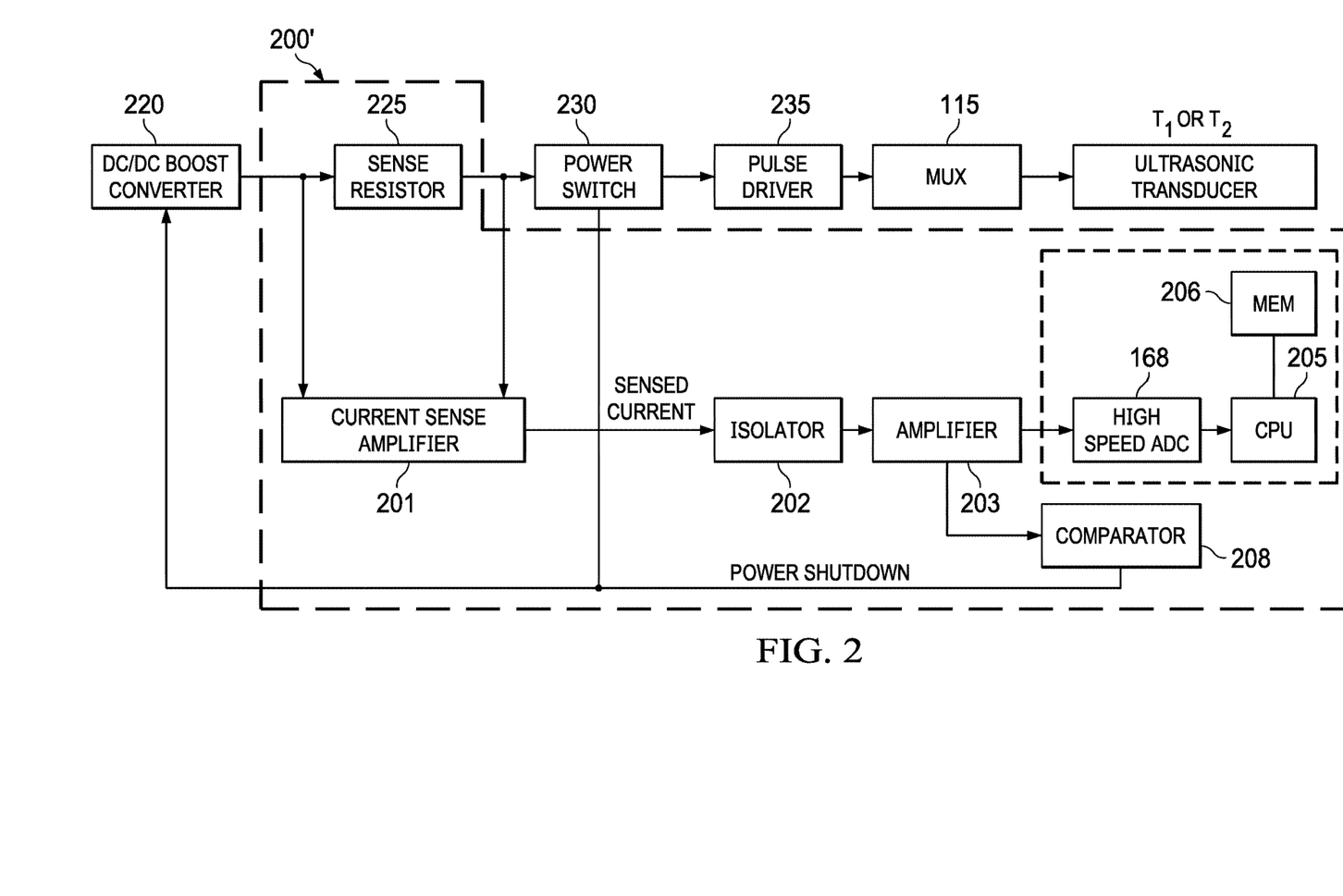
FIG. 2 is a block diagram representation of the respective components of an example current measurement circuit coupled to a portion of the transmitter of an ultrasonic transducer-based system or apparatus, according to an example aspect.

The USM 100 is shown including a current or voltage measurement circuit 200 proximate to or electrically coupled to sense the pulsed electrical signal, hereafter a "pulse signal", that is generally a pulsed current, flowing in the transmitter (Tx) 111. One way to sense the pulsed current is by adding a sense resistor 225 hooked in series within the Tx 111 as shown in FIG. 2 described below, where the voltage across the sense resistor 225 can be readily converted into a current using Ohm's law. Another example way to sense the pulsed current is by including a proximately located (non-contact) Hall-effect sensor that is a device used to measure the magnitude of a magnetic field that is generated by the pulsed current, where the level (amplitude) of pulsed current can be determined from the magnetic field that is measured.

The USM 100 is shown including an outer housing 108 also known as an enclosure having the ultrasonic transducer pair $T_1$ and $T_2$ therein on the same side of the pipe section of the pipeline 160, where $T_1$ and $T_2$ are spaced apart from one another by a distance shown as d, that implements a reflective path (indirect path) sensing configuration. The ultrasonic transducers $T_1$ and $T_2$ are shown including a matching layer 140 on the side of the piezoelectric elements 121 and 122 facing the pipe section, and a damping layer 127 is positioned on the piezoelectric elements 121 and 122 opposite the matching layer 140. There is an encapsulation layer 173 shown encapsulating both $T_1$ and $T_2$. The housing 108 can comprise a variety of different materials including brass, titanium, an aluminum alloy, or possibly a plastic depending on the application.

As known in acoustics, the thickness of a matching layer 140 is generally equal to one quarter of the acoustic wavelength ($\lambda/4$), to minimize the reflection at the front side of the matching layer 140, in favor of transmitted waves. Having found an optimum impedance value, the next determination is for finding a material having that particular impedance. For this purpose, one can use the known Mason Model which is a theoretical matching layer modeling algorithm. It is also possible to find a suitable thickness for the matching layer 140 by using a computer numerical simulation or comparative tests.

The damping layer 127 generally comprises a material with low density such as a porous foam or a polymer. The damping layer 127 may optionally also include a cancelling layer that also generally comprises a material with a low density, such as porous foam or a polymer.

The USM 100 is attached to the pipe section of the pipeline 160 generally either being inserted into the pipe section using a gas tight and high-pressure resistant mechanism, or configured as a clamp-on device installed on the outside of the pipe section. Although not shown in FIG. 1A, $T_1$ and $T_2$ may each have their own separate encapsulation chamber.

As noted above, the piezoelectric elements 121 and 122 generally employ piezoelectric crystals or piezoelectric ceramics, typically PZT, that are set into vibration when the pulsed signal (received from the Tx 111) is applied thereto, thereby generating ultrasonic waves. When the pulsed signal is applied to the piezoelectric elements 121, 122, the piezoelectric elements will resonate at a certain frequency at which its electrical impedance is at a minimum. Correspondingly, the drawn current in the Tx 111 is at a maximum. In operation, enabled by the digitally controlled multiplexer (MUX) 115, ultrasonic pulses are alternately transmitted by one of the piezoelectric elements 121, 122 of the ultrasonic transducers of the pair $T_1$ and $T_2$ and are received by the piezoelectric element of the other ultrasonic transducer of the pair needed for the flow measurement. When a single transducer is used for both Tx and Rx, the MUX 115 performs the function of a switch or a duplexer.

An angled axial signal path is shown in FIG. 1A by the dashed line inside the pipe section. As known in the art, the USM 100 can include more than the 2 ultrasonic transducers shown in FIG. 1A as $T_1$ and $T_2$, typically from two up to 16 ultrasonic transducers, or even more ultrasonic transducers depending on the pipe diameter. Although the USM 100 is shown including a separate Tx 111 and a receiver (Rx) 112, as an alternative to the separate Tx 111 and Rx 112 shown there can be a single transceiver, that are coupled to $T_2$ and $T_1$ respectively by the MUX 115 that enables the ultrasonic transducers $T_2$ and $T_1$ to swap (alternate) transmit and receive roles so that in one moment, Tx 111 is on, and the Rx 112 is on at another moment. The pipeline 160 in operation has a fluid therein, being a liquid or a gas, such as natural gas or hydrogen.

The USM 100 generally also includes a controller 120, typically comprising a microprocessor, digital signal processor (DSP), or a MCU, that has an associated memory shown as 'MEM' 124 that can store code for algorithms including algorithms for implementing disclosed methods as well as for a fluid velocity measurement. The controller 120 is coupled to the Tx 111 and the Rx 112, and is also coupled to control the MUX 115. The controller 120 also is configured to control the MUX 115 to switch the Tx and Rx roles in designated timing intervals.

Algorithms run by the controller 120 may be implemented by hardware and/or can be implemented by software. Regarding hardware-based implementations, algorithm equations can be converted into a digital logic gate pattern, such as using VHDL (a Hardware Description Language) that can then be realized using a programmable device such as a field-programmable gate array (FPGA) or complex programmable logic device (CPLD), or a dedicated application-specific integrated circuit (ASIC) to implement the logic gate pattern. Regarding software-based implementations, code for the algorithm is generally stored in a memory such as memory 124 that can be implemented by the controller 120.

The USM 100 as noted above is also shown including a current or voltage measurement circuit 200, as well as an RF unit 148, and a battery 178 that provides power for the respective active components of the USM 100 that require power. FIG. 2 described below shows an example current or voltage measurement circuit 200. The RF unit 148 is coupled to an antenna 149 that is outside of the housing 108 which enables the USM 100 to communicate over the air with one or more remote locations, typically for communicating with a control room. There is also a human-machine interface (HMI) 126 shown in FIG. 1A coupled to the controller 120 that may include a keyboard and a display for use by an operator or technician, if deemed needed. An operator or technician can use the HMI 126 to adjust operating parameters of the USM 100.

Figure 1B:
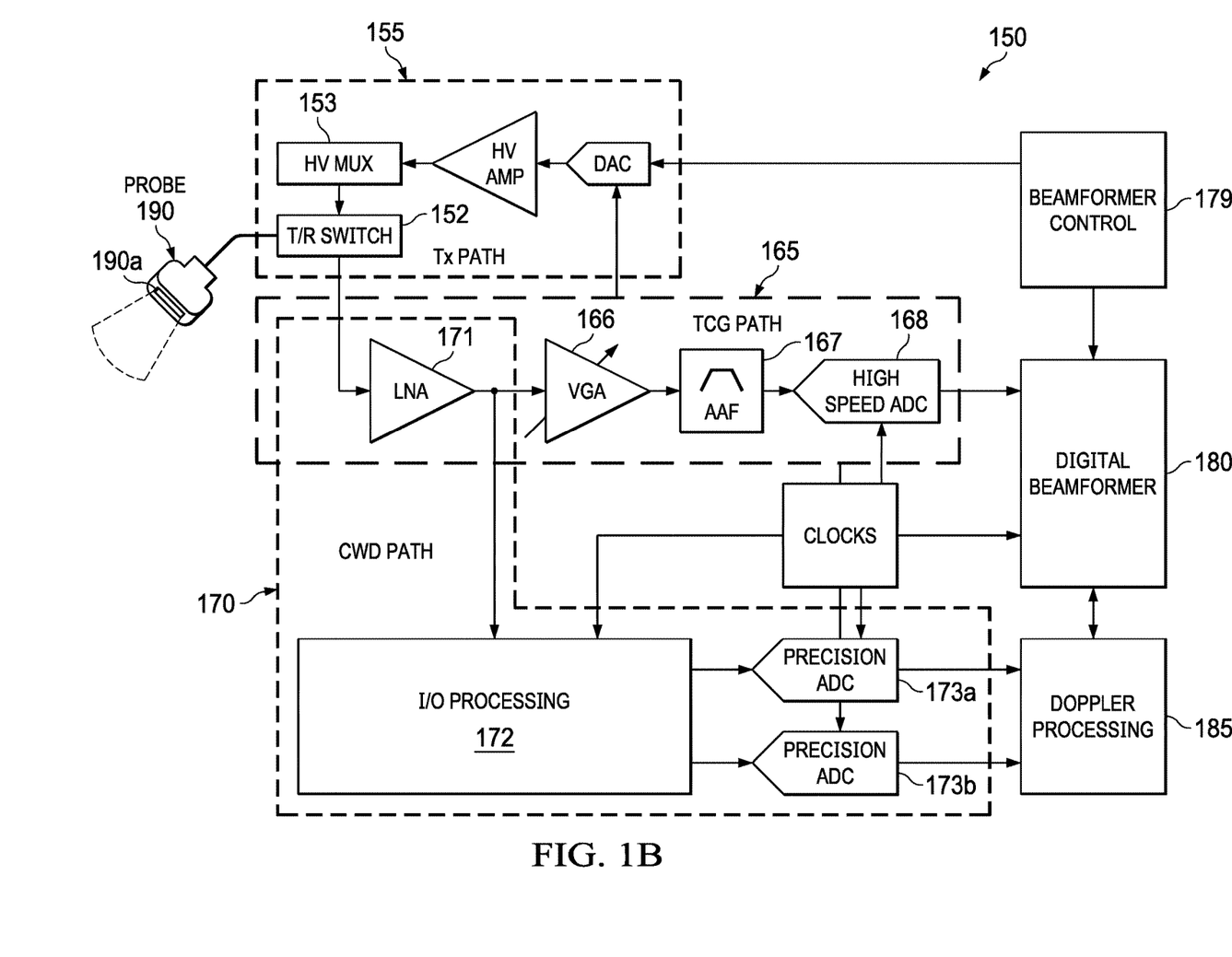
FIG. 1B is block diagram depiction of an example medical ultrasound imaging system for health monitoring. The probe shown includes an at least one ultrasonic transducer that is comprised of an array of piezoelectric elements that each transmit focused ultrasonic energy into the body and receive the resulting ultrasonic reflections.

FIG. 1B is block diagram depiction of an example medical ultrasound imaging system 150 for health monitoring. The probe 190 shown includes at least one ultrasonic transducer 190a that is comprised of an array of piezoelectric elements that each transmit focused energy into the body and receive the resulting reflections. Besides for ultrasound for medical imaging, in a NDT system there may be only one ultrasonic transducer that is controlled by a multiplexer or a T/R switch such as shown in FIG. 1B as 152 to work as an ultrasonic transmitter at a first instant of time, and then change a second instant of time to then be working as an ultrasonic receiver.

By transmitting acoustic energy into the body and receiving and processing the returning acoustic reflections, phased-array ultrasound systems can generate images of internal organs and structures, map blood flow and tissue motion, and also provide accurate blood velocity information. Conventionally, a large number of high-performance phased-array transmitters and receivers required to implement these medical imaging systems result in large and expensive implementations. Recently, advances in integration have allowed system designers to migrate to smaller, lower cost, and more portable ultrasound imaging system solutions with performance approaching these larger systems.

Although the medical ultrasound imaging system 150 shown having a single ultrasonic transducer 160a, a typical ultrasound imaging system uses a wide variety of ultrasonic transducers configured for specific diagnostic applications. Each ultrasound transducer comprises an array of piezoelectric transducers, such as comprising PZT, that transmit focused acoustic energy into the body and receive the resulting acoustic reflections. As known in the art, each piezoelectric element can be connected to other components in the medical ultrasound imaging system 150 with fine (small diameter) coaxial cables. Typical ultrasonic transducers 190a for the medical ultrasound imaging system 150 have 32 to as many as 512 piezoelectric elements, and generally operate at frequencies from 1 MHz to 15 MHz. Most medical ultrasound imaging systems provide two to as many as four switchable connectors to allow the clinician to easily switch among the various piezoelectric elements for each different examination type.

A typical phased-array ultrasound system will have from 32 to as many as 256 ultrasonic transmitters and receivers. In most cases, the ultrasound system will have fewer transmitters and receivers than the number of available piezoelectric elements. In these cases, high-voltage switches located in the ultrasonic transducer or the system are used as multiplexers to connect a specific transducer element to a specific transmitter/receiver (Tx/Rx) pair. In this way, the medical ultrasound imaging system 150 can dynamically change the active transducer aperture over the available array of transducer elements provided by the ultrasonic transducer 190a.

There is shown a Tx path 155 including a T/R switch 152 that is driven by a multiplexer shown as a high-voltage (HV) multiplexer 153. There is a time gain compensation (TCG) path 165 including a variable gain amplifier (VGA) 166 coupled to an antialiasing filter (AAF) 167 that is coupled to an ADC shown as a high-speed ADC 168. There is a continuous wave doppler (CWD) path 170 comprising a low noise amplifier (LNA) 171 between the T/R switch 152 and the VGA 166, and I/O processing 172 having an input coupled to an output of the LNA 171 and an output to ADCs shown a first precision ADC 173a and a second precision ADC 173b which have their respective outputs coupled to the Doppler processing block 185. The medical ultrasound imaging system 150 is shown including other blocks comprising a beamformer control 179, and a digital beamformer 180 that receives the high-speed ADCs 168 output signals which are typically routed through a high-speed Low-voltage differential signaling (LVDS) serial interface.

In spectral processing, the beamformed digital signals are digitally filtered, mixed to baseband by using quadrature local oscillators (LOs) at the transmit frequency, and then sampled at the transmit pulse repetition frequency (PRF). A fast Fourier transform (FFT) is generally then used to generate an output spectrum representing the velocity content of the signal. The signal magnitude for each bin of the FFT output is calculated and compressed to optimize the available, visible display dynamic range. The signal magnitude is then generally finally displayed versus time on a display (not shown).

Disclosed USM's such as USM 100 shown in FIG. 1A and other ultrasound-based systems such as medical ultrasound imaging system 150 shown in FIG. 1B, as well as disclosed methods, are able to distinguish the below-described 3 separate transducer problems recognized herein to all be significant possible problems for ultrasonic transducers. This first purpose is to identify an aging phenomenon for the piezoelectric element(s) in an early stage to enable generating an alarm to the customer/users (e.g., in the case of USM to a gas utility company or service of the supplier of the ultrasonic system), which enables a remedial action to be planned or taken for the ultrasonic transducer(s). For example, once alerted to this problem the ultrasonic transducer(s) can be replaced while remaining in the field on pre-scheduled time when the impact of downtime is minimal.

When the piezoelectric element(s) of the USM such as comprising PZT has aged, it is recognized that the piezoelectric element's electrical impedance can change, which will impact the drive current from the drive circuitry shown as Tx 111 in FIG. 1A applied to the piezoelectric elements, with the impedance generally increasing with aging which reduces the drive current. In case the piezoelectric element has a broken wire or loose solder to its electrodes, or a broken piezoelectric crystal, this can cause the drawn current from the Tx 111 to change to a minimal current, or no current in the case of an open circuit. This can indicate if a potted ultrasonic transducer hidden by an encapsulating material, such as being encapsulated by the encapsulation layer 173 shown in FIG. 1A, that cannot be checked from the outside, is connected properly, or not.

The second purpose is to identify the reason for abnormal attenuation of the received ultrasonic signal which can impact the measurement accuracy of the ultrasonic transducer-based system because a reduced signal amplitude reduces the signal-to-noise ratio (SNR) of the received signal. As noted above, the received signal amplitude can be evaluated to diagnose this problem. The third purpose is the protection against a short circuit failure caused by improper wiring (such as from a short or low impedance wire connection between the 2 terminals on the piezoelectric element (s) used for transducer cables), a piezoelectric element internal short, or improper soldering of wiring joints on the electrodes of the piezoelectric element(s). A short circuit, or related low resistance condition, in the case of being powered by a battery 178, will cause the battery 178 to be quickly discharged, which makes the lifetime of the battery 178 to be substantially shorter than expected.

FIG. 2 is a block diagram representation of the respective components of an example current or voltage measurement circuit shown as block 200 in FIG. 1A now shown as current or voltage measurement circuit 200' coupled to a portion of the Tx circuitry, according to an example aspect. The pulses are shown generated by a DC/DC boost power converter 220 coupled to one or more nodes of the Tx circuitry, where the DC/DC boost power converter 220 receives a source of DC power (not shown in FIG. 2 for simplicity), and at its input a suitable modulation signal, such as a pulse width modulation (PWM) signal to enable control of the width of the pulses that are outputted. The current or voltage measurement circuit 200' includes a sense resistor 225 connected in series between the DC/DC power converter 220 and the power switch 230. The power switch 230 is shown coupled to a pulse driver 235 that is coupled to a MUX 115 which is then coupled to the piezoelectric elements of the ultrasonic transducer shown as $T_1$ or $T_2$.

The current or voltage measurement circuit 200 comprises a current sense amplifier 201 connected across the sense resistor 225 used to amplify the current waveform that is coupled to an electrical isolator 202, that is coupled to an amplifier 203 that can be configured as a voltage follower. The amplifier 203 is shown connected to an input of a high-speed ADC 168, that may have two channels, where one channel can be used for the ultrasonic received signal, such as to determine the flow rate, and the other channel can be used for disclosed aspects including analyzing the waveform of the pulsed signal, where the output(s) of the high-speed ADC 168 is/are shown connected to the input of a central processing unit (CPU) 205 that can comprise a MCU. The CPU 205 has an associated memory shown as MEM 206.

The high-speed ADC 168 generally provides a sampling rate of generally at least 4 million samples per second (SPS). The current or voltage measurement circuit 200 captures the driving current waveform that is applied to the piezoelectric element(s) of the transmitter side ultrasonic transducer. Also shown as part of the current or voltage measurement circuit 200 is a comparator 208 that provides the function of short circuit protection. A reference voltage for the comparing operation performed by the comparator 208 is fixed and may be contained within a memory within the block shown as the comparator 208. The comparator 208 when triggered can send a power shutdown signal configured to turn off the DC/DC boost power converter 220, and a shutdown signal to also turn off the power switch 230.

This sensed pulsed signal can be processed by a CPU 205 utilizing its MEM 206 or by another computing device using a pattern checking algorithm that can utilize reference waveforms, such as obtained after the USM passes its functional test in the factory in which it is made, to examine the current waveform signal integrity. The CPU 205 will generally collect more than one current waveform, and check the respective current waveforms to the reference waveforms.

Figure 3:
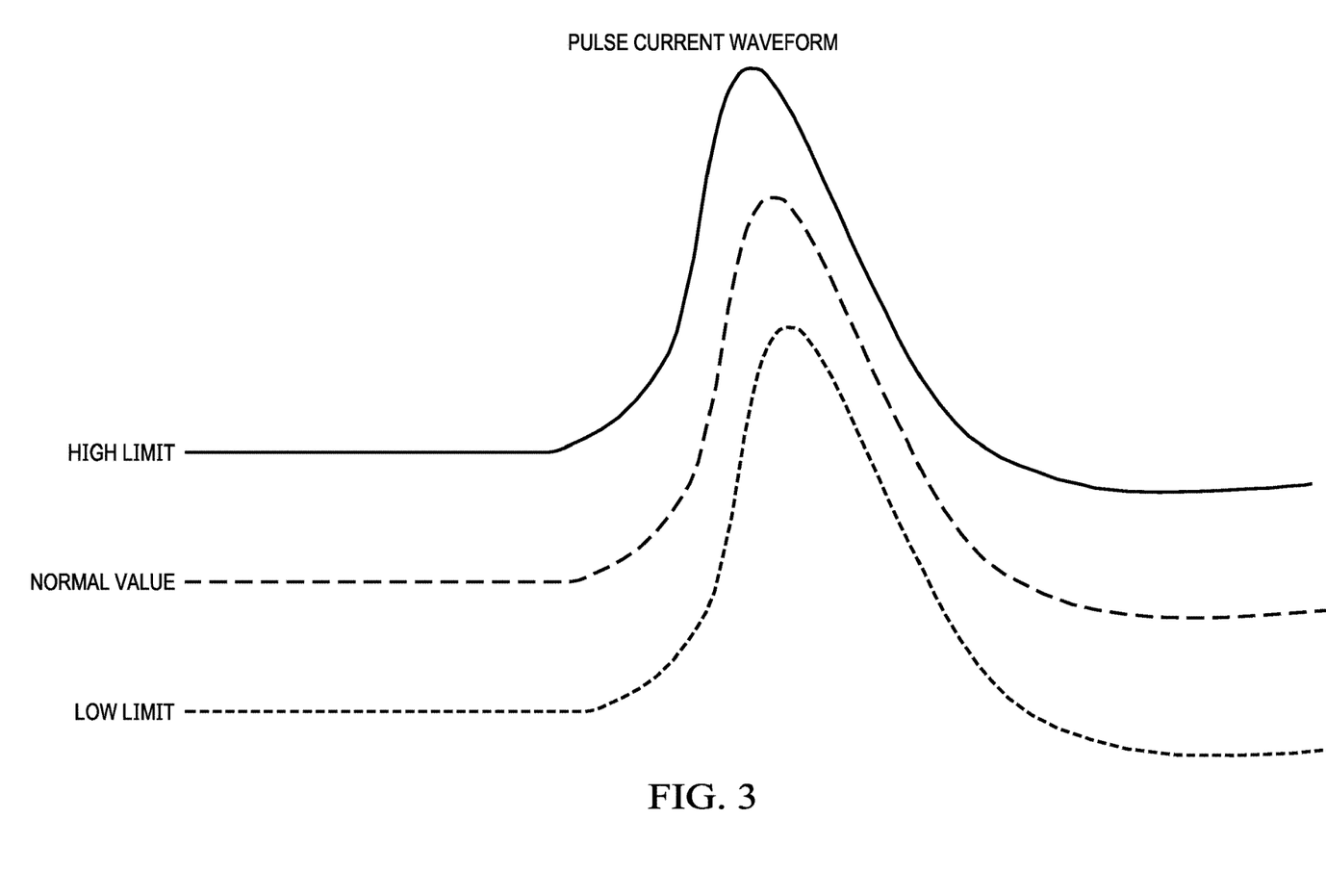
FIG. 3 shows example pulsed current waveform patterns illustrating a waveform having a high amplitude limit, a waveform having a low amplitude limit, and a waveform having a normal amplitude value.

FIG. 3 illustrates three example pulsed signal waveforms including a waveform shown as a high amplitude limit, a waveform shown as a normal amplitude value, and a waveform shown as a low amplitude limit. If the amplitude of sensed pulsed signal is outside the high amplitude limit and the low amplitude limit, this indicates that the impedance of the transmit piezoelectric element is abnormal, and is therefore at heightened risk of the above-described failure modes/problems including continuing the aging process likely leading to a later failure of the system.

If the sensed pulsed signal waveform is determined to be normal, it is possible that the receiver signal level may be relatively small as compared to an expected receiver signal level. The main reason for a relatively small receiver signal level can be a coating or a sticky fluid contamination layer deposited on the receiver side piezoelectric transducer's matching layer which as noted above is exposed to the fluid flowing in the pipeline. In this case, and alarm can be generated, which can comprise a wired or a wireless signal. Wire connections can include the RS485 communication standard used with a supervisory control and data acquisition (SCADA) system. The alarm may be sent to the gas utility company, or to a service center of the supplier, as a reminder to schedule preventative maintenance involving a cleaning of the ultrasonic transducer(s), particularly the relatively small diameter integrated flow tube (e.g., an integrated flow tube included for conventional sampling type USMs) included for measuring the gas flow rate flowing through the USM. The cleaning process is generally implemented as a manual process where the ultrasonic transducers or the USM are removed from the pipe section and then cleaned. Generally, according to worldwide regulations, gas pipes and flowmeters need to be in maintenance every two years, in which cleaning of the pipe is carried out as well.

Disclosed aspects will help monitor the health status of ultrasonic-based system such as USMs, and can as described above provide an alarm to alert the customer to clean the USM, such as an alarm sent using the RF unit 148 shown in FIG. 1A coupled to the antenna 149 to wirelessly transmit the alarm. Regarding the above-described third problem, a disclosed current or voltage monitor circuit can also trigger an over current protection alert to enable remedial action to be taken that increases the reliability of the USM.

Figure 4:
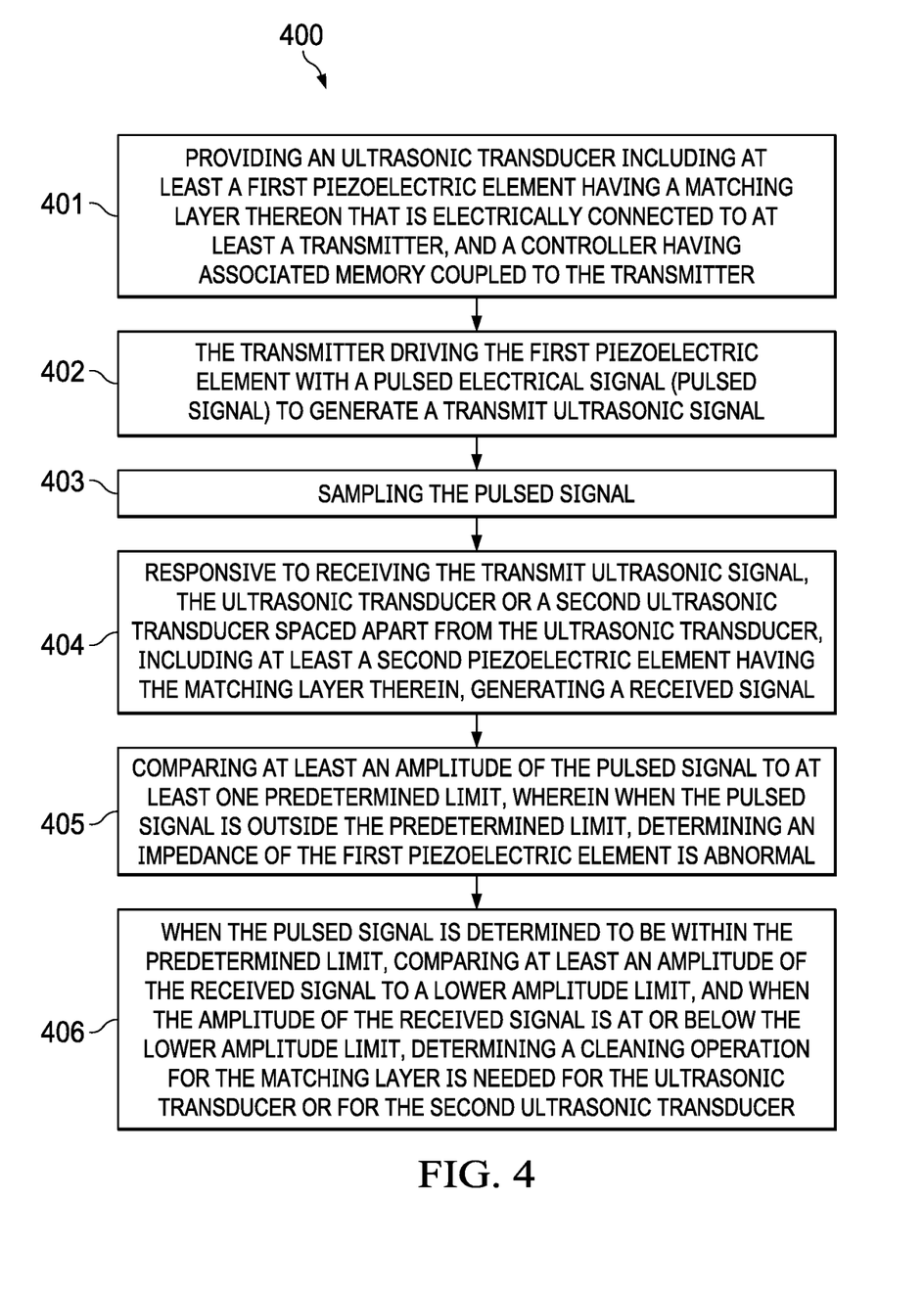
FIG. 4 is a flowchart showing steps in an example method of monitoring the health of an ultrasonic transducer of an ultrasonic-based system or apparatus.

FIG. 4 is a flowchart showing steps in an example method 400 of monitoring ultrasonic transducer of an ultrasonic-based system. Step 401 comprises providing an ultrasonic transducer including at least a first piezoelectric element having a matching layer thereon that is electrically connected to at least a transmitter, and a controller having associated memory coupled to the transmitter. Step 402 comprises the transmitter driving the first piezoelectric element with a pulsed electrical signal (pulsed signal) to generate a transmit ultrasonic signal. Step 403 comprises sampling the pulsed signal. Step 404 comprises responsive to receiving the transmit ultrasonic signal, the ultrasonic transducer or a second ultrasonic transducer spaced apart from the ultrasonic transducer including at least a second piezoelectric element also having the matching layer thereon generating a received signal.

Step 405 comprises comparing at least an amplitude of the pulsed signal to at least one predetermined limit, wherein when the pulsed signal is outside the predetermined limit, determining an impedance of the first piezoelectric element is abnormal. Step 406 comprises when the pulsed signal is determined to be within the predetermined limit, comparing at least an amplitude of the received signal to a lower amplitude limit, wherein when the amplitude of the received signal is at or below the lower amplitude limit, determining a cleaning operation for the matching layer is needed for the ultrasonic transducer or for the second ultrasonic transducer.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A method of monitoring a first ultrasonic transducer of an
    ultrasonic-based system, wherein
        the first ultrasonic transducer comprising at least a first piezoelectric element comprising a first matching layer thereon being electrically connected to at least a transmitter, a controller with an associated memory coupled to the transmitter, wherein the method comprising:

driving, by the transmitter, the first piezoelectric element with a pulsed electrical signal to generate a transmit ultrasonic signal;
sampling the pulsed electrical signal;
responsive to receiving the transmit ultrasonic signal, a second ultrasonic transducer including at least a second piezoelectric element that is spaced apart from the first ultrasonic transducer comprising a second matching layer thereon generating a pulsed waveform signal,
wherein the second piezoelectric element is different from the first piezoelectric element;
comparing an amplitude of the pulsed electrical signal to at least one predetermined limit, wherein when the amplitude of the pulsed electrical signal is outside the at least one predetermined limit, determining an impedance of the first piezoelectric element is abnormal or an impedance of the second piezoelectric element is abnormal; and
when the amplitude of the pulsed electrical signal is determined to be within the at least one predetermined limit, comparing an amplitude of the pulsed waveform signal to a lower amplitude limit, wherein when the amplitude of the pulsed waveform signal is at or below the lower amplitude limit, comparing a shape of the pulsed waveform signal to at least one waveform shape reference, wherein when the shape of the pulsed waveform signal is determined to be different as compared to the at least one waveform shape reference, determining the impedance of the first piezoelectric element is abnormal due to deposition of a contamination layer on the first matching layer or the impedance of the second piezoelectric element is abnormal due to deposition of the contamination layer on the second matching layer, and generate an alert to clean the first matching layer of the first ultrasonic transducer or to clean the second matching layer of the second ultrasonic transducer.

2. The method of claim 1, wherein the ultrasonic-based system consists of the first ultrasonic transducer as only a single ultrasonic transducer, and wherein the ultrasonic-based system, further comprises a duplexer positioned between the controller and the single ultrasonic transducer is for controlling the first ultrasonic transducer to switch between transmitting and receiving.

3. The method of claim 1, wherein the pulsed electrical signal comprises a pulsed current or a pulsed voltage, and wherein the transmitter further comprises a current or voltage measurement circuit for the sampling of the pulsed current or the pulsed voltage.

4. The method of claim 3, wherein the current or voltage measurement circuit includes a sense resistor in series with the transmitter, and wherein the sampling comprises sensing across the sense resistor.

5. The method of claim 1, wherein the pulsed electrical signal comprises a pulsed current, and a current or voltage measurement circuit comprising a Hall-effect current sensor positioned for sampling of the pulsed current.

6. The method of claim 1, further comprising generating and transmitting the alert responsive to either the determining the impedance of the first piezoelectric element is abnormal or the determining a cleaning operation is needed for the first ultrasonic transducer or the second ultrasonic transducer.

7. The method of claim 1, wherein the ultrasonic-based system comprises an ultrasonic flowmeter, and wherein the ultrasonic flowmeter is installed on a pipe section of a pipeline.

8. The method of claim 1, wherein the first piezoelectric element comprises an array of piezoelectric elements, and wherein the ultrasonic-based system comprises an ultrasonic imaging system.

9. The method of claim 1, wherein the predetermined limit comprises both a high limit and low limit.

10. An ultrasonic-based system, comprising:
a transmitter and a receiver;
an ultrasonic transducer including at least one piezoelectric element having a matching layer thereon electrically connected to at least the transmitter,
a controller having an associated memory coupled to the transmitter;
the transmitter driving the piezoelectric element with a pulsed electrical signal that comprises a pulsed current or a pulsed voltage;
a current or voltage measurement circuit coupled to at least one node in the transmitter for sampling the pulsed electrical signal;
wherein in response to the pulsed electrical signal the piezoelectric element transmits a transmit ultrasonic signal;
the controller with an associated memory storing code for implementing an algorithm for monitoring the ultrasonic transducer wherein the controller is configured to:
compare an amplitude of the pulsed electrical signal sensed by the current or voltage measurement circuit by sampling the pulsed electrical signal to at least one predetermined limit, wherein when the amplitude of the pulsed electrical signal is determined to be outside the at least one predetermined limit, determining an impedance of the piezoelectric element is abnormal; and
when the amplitude of the pulsed electrical signal is within the at least one predetermined limit, comparing an amplitude of a pulsed waveform signal generated by the ultrasonic transducer to a lower amplitude limit, wherein when the amplitude of the pulsed waveform signal is at or below the lower amplitude limit, comparing a shape of the pulsed waveform signal to at least one waveform shape reference, wherein when the shape of the pulsed waveform signal is determined to be different as compared to the at least one waveform shape reference, determining the impedance of the piezoelectric element is abnormal due to deposition of a contamination layer on the matching layer, and generating an alert for cleaning the matching layer of the ultrasonic transducer.

11. The ultrasonic-based system of claim 10, wherein the ultrasonic-based system consists of the ultrasonic transducer as only a single ultrasonic transducer, and wherein the ultrasonic-based system, further comprises a duplexer positioned between the controller and the single ultrasonic transducer for controlling the ultrasonic transducer to switch between transmitting and receiving.

12. The ultrasonic-based system of claim 10, wherein the current or voltage measurement circuit includes a sense resistor in series with the transmitter, and wherein the sampling comprises sensing across the sense resistor.

13. The ultrasonic-based system of claim 10, comprising generating and transmitting the alert responsive to either the determining the impedance of the piezoelectric element is abnormal or the determining a cleaning operation is needed for the matching layer.

14. The ultrasonic-based system of claim 10, wherein the ultrasonic transducer further comprises an encapsulation layer.

15. The ultrasonic-based system of claim 10, wherein the at least one piezoelectric element comprises an array of piezoelectric elements, and wherein the ultrasonic-based system comprises an ultrasonic imaging system.

16. An ultrasonic flowmeter (USM), comprising:
an outer housing having an attachment feature for attaching to a pipe section of a pipeline that is adapted for having a fluid flowing therein;
a first ultrasonic transducer comprising at least a first piezoelectric element and at least a second ultrasonic transducer comprising at least a second piezoelectric element, the first piezoelectric element comprising a first matching layer and the second piezoelectric elements comprising a second matching layer thereon;
a transmitter and a receiver coupled by a multiplexer to the first ultrasonic transducer and the second ultrasonic transducer;
a controller having an associated memory coupled to the transmitter;
the transmitter for driving the first ultrasonic transducer with a pulsed electrical signal;
a current or voltage measurement circuit coupled to at least one node in the transmitter for sampling the pulsed electrical signal;
wherein in response to the pulsed electrical signal the first ultrasonic transducer transmitting a transmit ultrasonic signal;
the controller having an associated memory storing code for implementing an algorithm for monitoring each of the first ultrasonic transducer and the second ultrasonic transducer, wherein the controller is configured to:
compare an amplitude of the pulsed electrical signal sensed by the current or voltage measurement circuit by sampling the pulsed electrical signal to at least one predetermined limit, wherein when the amplitude of the pulsed electrical signal is determined to be outside the at least one predetermined limit, determining an impedance of the first piezoelectric element or an impedance of the second piezoelectric element is abnormal; and
when the amplitude of the pulsed electrical signal is within the at least one predetermined limit, comparing an amplitude of a pulsed waveform signal generated by the second ultrasonic transducer to a lower amplitude limit, wherein when the amplitude of the pulsed waveform signal is at or below the lower amplitude limit, comparing a shape of the pulsed waveform signal to at least one waveform shape reference, wherein when the shape of the pulsed waveform signal is determined to be different as compared to the at least one waveform shape reference determining the impedance of the first piezoelectric element is abnormal due to deposition of a contamination layer on the first matching layer or determining the impedance of the second piezoelectric element is abnormal due to deposition of the contamination layer on the second matching layer, and, generating an alert for cleaning the first matching layer of the first ultrasonic transducer or for cleaning the second matching layer of the second ultrasonic transducer.

17. The USM of claim 16, wherein the current or voltage measurement circuit includes a sense resistor in series with the transmitter, and wherein the sampling comprises sensing across the sense resistor.

18. The USM of claim 16, comprising generating and transmitting the alert responsive to either the determining the impedance of the first piezoelectric element or the second piezoelectric element is abnormal, or the determining a cleaning operation is needed for the first matching layer of the first ultrasonic transducer or the second ultrasonic transducer.

* * * * *